(12) United States Patent
Egger et al.

(10) Patent No.: US 7,763,026 B2
(45) Date of Patent: Jul. 27, 2010

(54) SAW JIG FOR MEDICAL PURPOSES

(75) Inventors: Berthold Egger, Stockach (DE); Rudiger Beck, Stockach (DE)

(73) Assignee: Karl Storz GmbH & Co. KG (DE)

( * ) Notice: Subject to any disclaimer, the term of this patent is extended or adjusted under 35 U.S.C. 154(b) by 1160 days.

(21) Appl. No.: 10/918,178

(22) Filed: Aug. 13, 2004

(65) Prior Publication Data

US 2005/0070909 A1    Mar. 31, 2005

Related U.S. Application Data

(63) Continuation of application No. PCT/EP03/00813, filed on Jan. 28, 2003.

(30) Foreign Application Priority Data

Feb. 13, 2002    (DE)  ................................ 102 05 799

(51) Int. Cl.
*A61F 5/00*    (2006.01)
(52) U.S. Cl. ........................................................ 606/87
(58) Field of Classification Search ............. 606/87–89; 144/379
See application file for complete search history.

(56) References Cited

U.S. PATENT DOCUMENTS

| 542,738 | A | * | 7/1895 | Levan | 83/760 |
|---|---|---|---|---|---|
| 886,238 | A | * | 4/1908 | McCune | 83/766 |
| 1,208,150 | A | * | 12/1916 | Hall | 83/767 |
| 3,872,761 | A | * | 3/1975 | Gutowski et al. | 83/767 |
| 4,440,168 | A | * | 4/1984 | Warren | 606/102 |
| 4,502,474 | A | | 3/1985 | Comparetto | 128/92 |
| 4,627,425 | A | * | 12/1986 | Reese | 606/87 |
| 4,638,700 | A | * | 1/1987 | Fushiya et al. | 83/468.3 |
| 4,750,481 | A | | 6/1988 | Reese | 128/92 |
| 4,952,213 | A | * | 8/1990 | Bowman et al. | 606/79 |
| 5,075,976 | A | * | 12/1991 | Young | 30/391 |
| 5,275,603 | A | * | 1/1994 | Ferrante et al. | 606/86 R |
| 5,364,401 | A | * | 11/1994 | Ferrante et al. | 606/84 |
| 5,470,335 | A | | 11/1995 | Du Toit | 606/73 |
| 5,601,565 | A | | 2/1997 | Huebner | 606/87 |
| 5,911,724 | A | | 6/1999 | Wehrli | 606/88 |

FOREIGN PATENT DOCUMENTS

DE    195 16 294 A1    7/1996

\* cited by examiner

*Primary Examiner*—Anu Ramana
(74) *Attorney, Agent, or Firm*—St. Onge Steward Johnston & Reens LLC

(57) ABSTRACT

A saw guide for medicinal purposes is provided, having a handle and a sawblade guide element mounted on the handle to receive and guide a sawblade, said sawblade guide element including a frame mounted on the handle and a guide recess for the sawblade, mounted rotatably in the frame. The sawblade guide element can be secured on the material being sawed and can be adjusted in the position fixed at various end positions on the saw material. The frame is configured as a circle segment open on one side, into which the guide recess, which has an essentially circular base body, can be inserted in a form-locking connection. A stud is configured on the base body extending radially outward and having at least one essentially vertical slit for receiving the sawblade.

18 Claims, 2 Drawing Sheets

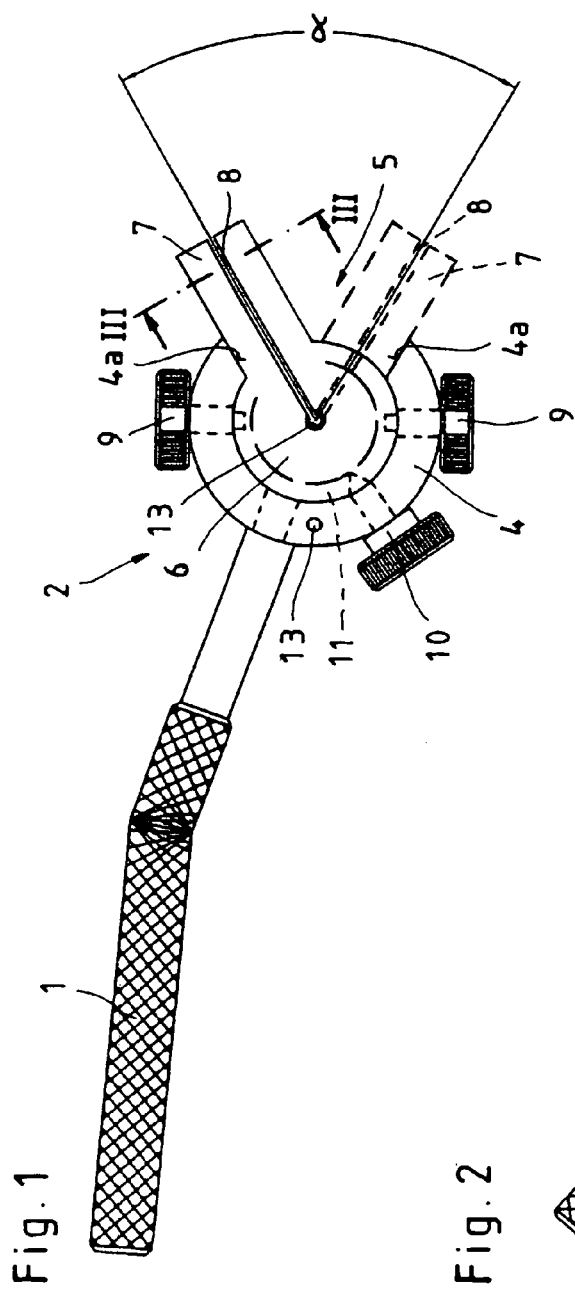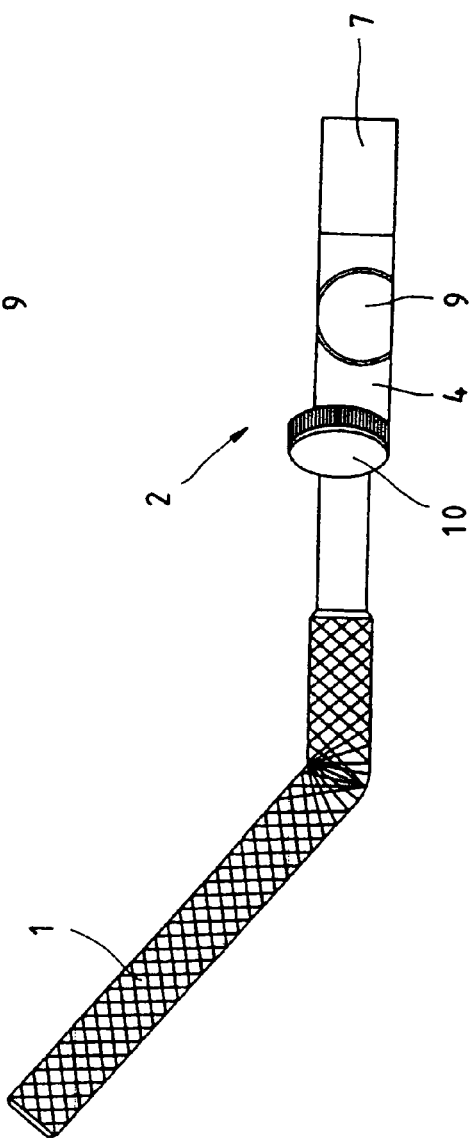
Fig.1
Fig.2

SAW JIG FOR MEDICAL PURPOSES

CROSS-REFERENCE TO RELATED APPLICATIONS

This application is a continuation of pending International Patent Application No. PCT/EP03/00813 filed Jan. 28, 2003 which designates the United States and claims priority of pending German Application No. 102 05 799 filed Feb. 13, 2002.

FIELD OF THE INVENTION

The invention relates to a saw guide for medical purposes, with a handle and a sawblade guide element mounted on the handle to receive and guide a sawblade, wherein the sawblade guide element consists of a frame mounted on the handle and a guide recess for the sawblade mounted rotatably in the frame, and wherein the guide element can be secured on the material being sawed and can be adjusted in the position fixed at various notches on the saw material.

BACKGROUND OF THE INVENTION

Saw guides are used to guide the sawblade of the saw in a sawing procedure at an exactly calculated angle to the saw material that is to be sawed. Such an exact guidance of the sawblade is particularly important with saw guides for medicinal purposes when, for instance in Hallux valgus operating procedures to remove stress deformations in the region of the large toe, bones must be cut by means of a saw.

A generic saw guide for medical purposes is described, for instance, in U.S. Pat. No. 5,911,724 A. In this familiar saw guide, the sawblade guide element consists of a frame that can be secured on the material to be sawed, a goniometer connected with the frame, and a sawblade guide that can be movably secured on the goniometer by means of a rotation arm. This familiar saw guide allows the adjustment of various saw notches, but the saw guide is fixed on the saw material; yet, this known device consists of many separately adjustable components, which, on the one hand, complicate the fixing and adjustment and, on the other hand, by their reciprocal play, make an exact guidance of the sawblade more difficult.

Another fork saw guide for medical purposes, known in the practice of the Hallux valgus operating procedure, can be secured by means of a wire on the bones to be treated. The fork-shaped sawblade guide allows the sawblade to be directed, but the surgeon must determine and hold the angle settings himself, so that a precise formation of a saw cutting procedure, for instance one of wedge shape, is hardly practicable.

BRIEF SUMMARY OF THE INVENTION

The objective of the present invention therefore is to provide a saw guide for medical purposes that is simple to operate and that ensures an exact, precisely located direction of the sawblade.

This objective is fulfilled by means of the invention in that the frame is configured as a circle segment open on one side, into which the guide recess, which has an essentially circular-shaped base body, can be inserted in a form-locking connection. Additionally, a stud is configured on the base body extending radially outward, having at least one essentially vertical slit for receiving the sawblade.

By means of the inventive design, the surgeon for the first time has a saw guide available which ensures a constantly exact and precisely located direction of the sawblade and which allows the adjustment of various cutting positions while maintaining the position of the frame fixed to the material being sawed.

The slit configured in the stud for receiving the sawblade extends advantageously as far as the middle of the base body.

In order to allow the insertion of a sawblade with limited saw teeth in the guiding slit of the guide recess, without having the saw teeth wedged into the saw guide, the slit is configured to be wider in the area of the saw teeth of the sawblade.

The angle of aperture of the frame, having the shape of an open circle segment, is less than 180 degrees in order to ensure a guiding position of the guide recess in the frame. When the guide recess is in such guiding position, the frame surrounds the guide recess by more than half of its peripheral surface. The angle of aperture is advantageously 60 degrees.

In order to be able to guide and position the guide recess in the frame, at least one guide element and at least one stop element are positioned on the frame. According to a practical embodiment, in the radially outward-facing peripheral surface of the base body at least one groove is mounted on the frame for receiving one guide element at a time, and advantageously two guide elements are situated essentially opposite to one another and the at least one guide element is configured as screws that can be screwed into the frame in such a way that the free end of the screws extending through the frame engages in the groove of the base body for guiding purposes.

For precise positioning of the guide recess within the frame, the guide recess can be secured in the particular rotation position inside the frame by means of a stop element configured as a locking screw.

The angle of rotation of the guide recess inside the frame is restricted by the contact of the stud with the front surface on both sides of the aperture of the frame. Therefore, the angle of aperture of the frame is advantageously selected so that it corresponds to the cutting angle to be executed. This ensures that the surgeon will perform a constantly exact sawing incision in a simple manner by means of the cutting positions being adjusted rotatably in nailing positions.

The saw guide is fixed to the sawing material by at least one securing element, which according to a first embodiment of the invention has a through-borehole configured on the frame and/or on the guide recess, especially on the base body. A holding pin, especially a wire, can be inserted into this borehole, extending all the way into the sawing material. Advantageously, the saw guide can be secured by means of at least two fixing elements on the sawing material in order to prevent turning of the saw guide.

According to a second embodiment of the invention, it is proposed that the fixing element is configured as a fixing pin that can be mounted on the frame and/or on the guide recess, especially on the base body, and that is fixable on the sawing material.

The determination of new cutting angles is facilitated by the fact that the frame is mounted removably on the handle, so that by simply exchanging the frame the saw guide can be outfitted with new angles of attack.

It is further proposed that the handling of the inventive saw guide is facilitated by the fact that the handle is configured as a rod-shaped handle that is arranged at an angle to the sawblade guide element both in the horizontal and the vertical directions.

It is finally proposed that the surface of the handle, at least the distal part of the handle, has a milled finish in order to improve grippability of the handle by the surgeon.

Additional characteristics and advantages of the invention are explained with the help of the related drawings, in which the embodiment of an inventive saw guide is illustrated in schematic, exemplary fashion.

BRIEF DESCRIPTION OF THE DRAWINGS

FIG. 1 shows an overview of a saw guide according to the invention.

FIG. 2 shows a 90 degree side view of the saw guide from FIG. 1.

DETAILED DESCRIPTION OF THE INVENTION

Figure 4:
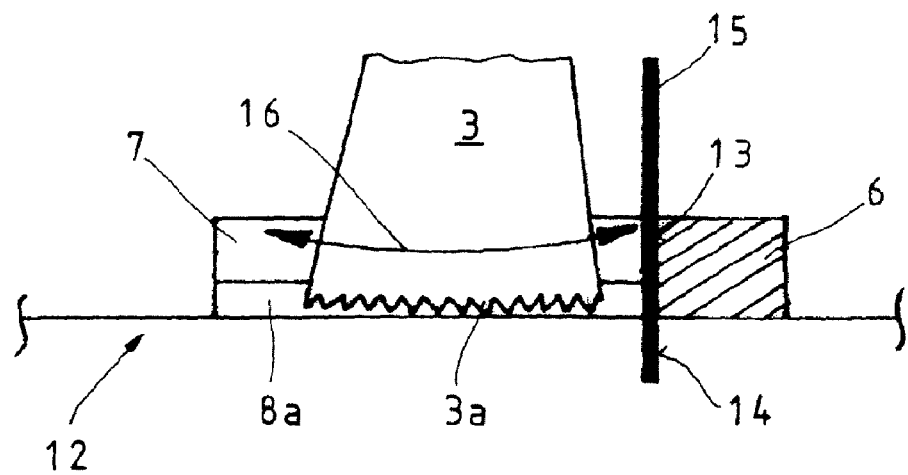
FIG. 4 shows a partially cut-out detailed schematic side view of a saw guide according to the invention with inserted saw blade.

The saw guide illustrated in FIGS. 1 and 2 consists essentially of a handle 1 for guiding and holding the saw guide as well as a sawblade guide element 2 mounted on the handle 1 for mounting and guiding a sawblade 3, as shown in FIG. 4. For improved ease of handling, the handle 1, as can be seen from FIG. 1, is turned at an angle to the sawblade guide element 2, and even twice in the illustrated embodiment, namely in the horizontal and the vertical direction with respect to the extension of the sawblade guide element 2. In addition, the surface of the handle 1, at least in the distal gripping area, is configured with a border in order to increase the grippability of the rod-shaped handle 1.

The sawblade guide element 2, as illustrated in FIG. 1, consists of a frame 4 that is open on one side and is shaped like a segment of a circle, and of a guide recess 5 that is rotatably inserted in a form-locking connection in the frame 4. The guide recess 5 consists of an essentially circular-shaped base body 6 and a stud 7 extending radially outward from the base body 6. As can be seen from FIG. 1, the aperture angle alpha of the frame 4 is less than 180 degrees so that the frame 4 surrounds the base body 6 of the guide recess 5 at least to the extent that the guide recess 5 is held inside the frame 4 and can be removed or inserted into it only in the vertical direction. In the illustrated embodiment of the frame 4 the aperture angle alpha is 60 degrees.

Figure 3:
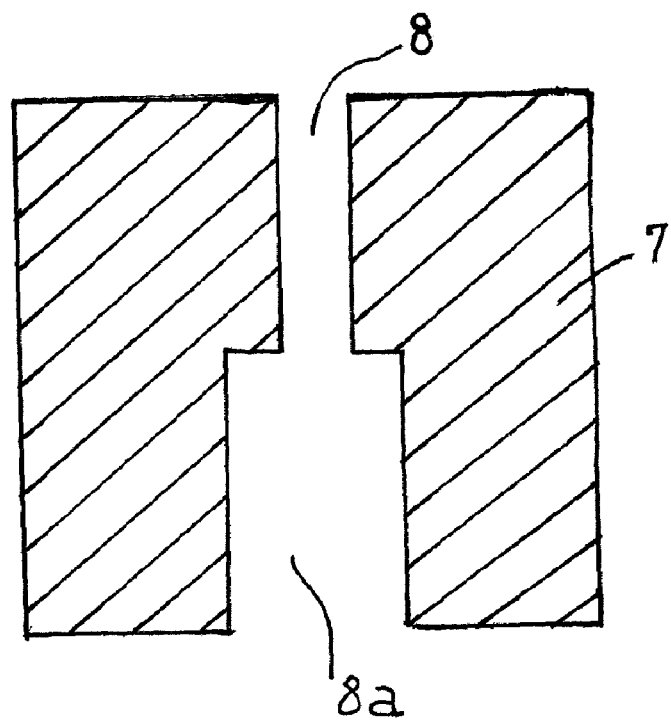
FIG. 3 shows a cutout along the line III-III as in FIG. 1.

The guide recess 5 has a slit 8 extending from the free end of the stud 7 to the middle of the base body 6 for receiving and guiding the sawblade 3. In order to be able to insert a sawblade 3 with partially configured saw teeth 3a, that is teeth protruding slightly laterally outward, into the slit 8 and to be able to guide it in this slit, the slit 8 has a lower area 8a into which the saw teeth 3a are inserted that is wider in configuration than the upper area, as can be seen from the cutout view in FIG. 3.

The guide recess 5 can be guided and positioned with precision inside the frame 4 by means of at least one guide element 9 positioned on the frame 4 and at least one stop element 10 positioned on the frame 4. In the illustrated embodiment of the saw guide, there are two screws provided as guide elements 9 and situated opposite to one another on the frame 4 where they can be screwed into the frame 4; their free ends extending through the frame 4 engage in a groove 11 formed in the radial surrounding surface of the base body 6 in such a way that the guide recess 5, on the one hand, is held securely inside the frame 4 in vertical direction while, on the other hand, it remains rotatably mounted inside the frame 4.

While the guide elements 9 serve exclusively to mount the guide recess 5 rotatably inside the frame 4, the guide recess 5 is precisely positioned and immovably secured by means of the stop element 10 configured as a locking screw. Thus, by means of the stop element 10 the guide recess 5 can be firmly clamped in its rotation position inside the frame 4. The angle of rotation of the guide recess 5 inside the frame 4 is restricted by the stud 7 coming in contact with the front ends 4a of the frame 4, as can be seen from the illustration in FIG. 1, in which both end positions of the rotation area of the guide recess 5 are shown. The aperture angle alpha of the frame 4 is advantageously selected in such a way that it corresponds to the wedge-shaped saw cuts to be performed by the surgeon, so that in order to select the correct cutting positions the surgeon has to rotate the guide recess 5 each time only until it comes in contact with one of the front ends 4a of the frame 4, in order to select the exactly positioned placement for completing the sawing incision.

The illustrated saw guide is used as follows:

Before the operation, the surgeon determines the size of the wedge of the sawing material to be resectioned and secures a frame 4 with a corresponding aperture angle alpha of the handle 1. Then the surgeon positions the saw guide by means of the handle 1 on the sawing material, such as a bone 12, as shown in FIG. 4, and fixes the saw guide in the precise location on the bone 12 that is to be operated on, while the guide recess 5 happens to be in a nailing position in which the stud 7 is in contact with a front end 4a of the frame 4.

To fix the saw guide on the sawing material (bone 12), the saw guide in accordance with the illustrated embodiment has two through-boreholes 13, which are configured, on the one hand, in the frame 4 and, on the other hand, in the middle of the base body 6 of the guide recess 5. Through these through-boreholes 13, holding pins, for instance wires 15, extending to the corresponding boreholes 14 in the bone 12, are inserted, and by means of these pins the saw guide can be fixed in an exact position on the bone 12 as seen in FIG. 4 in the example of the through-borehole 13 in the middle of the base body 6 of the guide recess 5.

It is also possible of course to position fixing stems, for instance, on the underside of the frame 4 and/or of the guide recess 5, which can penetrate into the sawing material.

After fixing the saw guide on the bone 12, the surgeon guides the sawblade 3 from the free end of the stud 7 into the slit 8 in such a way that the advantageously restricted saw teeth 3a are mounted in the lower, broader area 8a of the slit 8, as can also be seen from FIG. 4. The sawblade 3 is inserted so far into the slit 8 that it comes into contact with the wire 15. Now, by carrying out a sawing motion in the direction of the arrow 16, the surgeon can perform the first sawing cut of the wedge that is to be resectioned. Then the surgeon draws the sawing material 3 once more over the free end of the stud 7 out of the slit 8.

By opening the stop element 10 configured as a locking screw, the guide recess can now be rotated into the second nailing position shown with broken lines in FIG. 1, in which position the stud 7 comes into contact with the other surface 4a of the frame 4. Now the sawblade 3 is again inserted into the slit 8 and the second saw cutting, which completes the wedge to be resectioned, is carried out.

After the sawblade 3 is pulled out of the guide recess 5 and the saw guide is released from the bone 12, the surgeon receives an exactly sawed wedge, with spreading angle corresponding exactly to the angle of aperture alpha of the frame 4.

A saw guide of this design, in a simple and safe manner, permits an exact guidance and positioning of the sawblade 3, so that the surgeon is ensured simple handling and can always perform an exact saw cutting.

In addition, the described saw guide is distinguished by the fact that it can be completely disassembled simply and quickly for cleaning purposes.

What is claimed is:

1. A saw guide for medical purposes, comprising
a handle; and
a sawblade guide element mounted on the handle to receive and guide a sawblade;
wherein the sawblade guide element comprises a frame mounted on the handle and a guide receptacle for the sawblade mounted rotatably in the frame, and wherein said sawblade guide element can be secured on the material to be sawn and can be adjusted in a position fixed on the material to be sawn to different saw cuts;
wherein the frame is configured as a circle segment which has an opening on one side and into which the guide receptacle, which has an essentially circular-shaped base body, can be inserted in a form-locking connection;
wherein a stud is configured on the base body extending radially outward from the base body and having at least one slit that extends along a longitudinal axis of the stud for receiving the sawblade; and
wherein at least one positioning element and at least one stop element are configured on the frame to guide and position the guide receptacle, wherein in a peripheral surface of the base body pointing radially outward at least one groove is configured to receive one positioning element at a time that is mounted on the frame.

2. The saw guide according to claim 1, wherein the slit extends to the middle of the base body.

3. The saw guide according to claim 1, wherein the slit for receiving the sawblade is designed broader in the area adjacent to the material to be sawn.

4. The saw guide according to claim 1, wherein the opening of the frame is defined by an arc subtending an angle less than 180 degrees.

5. The saw guide according to claim 1, wherein two positioning elements are mounted essentially opposite to one another.

6. The saw guide according to claim 1, wherein the at least one positioning element is configured as a screw that can be screwed into the frame in such a way that a free end of the screw extending through the frame engages in the groove of the base body.

7. The saw guide according to claim 1, wherein the guide receptacle can be secured in the particular rotation position inside the frame by means of a stop element configured as a locking screw.

8. The saw guide according to claim 1, wherein the rotation angle of the guide receptacle inside the frame is restricted by the stud contacting both sides of the front end of the opening of the frame.

9. The saw guide according to claim 1, wherein the guide element can be secured by at least one fixing element on the material to be cut.

10. The saw guide according to claim 9, wherein the fixing element is configured as a through-borehole provided on the base body, said borehole being configured to receive a wire configured as a stop pin-extending into the material to be cut.

11. The saw guide according to claim 9, wherein the fixing element is configured as a fixing pin mounted on the base body, and which fixing pin can be secured on the material to be cut.

12. The saw guide according to claim 9, wherein the fixing element is configured as a through-borehole on the frame, said borehole being configured to receive a wire configured as a stop pin extending into the saw material.

13. The saw guide according to claim 9, wherein the fixing element is configured as a fixing pin mounted on the frame, and which can be secured on the saw material.

14. The saw guide according claim 1, wherein the frame is mounted exchangeably on the handle.

15. The saw guide according to claim 1, wherein the handle is configured as a rod-shaped grip that is positioned at an angle to the sawblade guide element.

16. The saw guide according to claim 15, wherein the handle is positioned at an angle relative to the sawblade guide element both in the horizontal and in the vertical direction.

17. The saw guide according to claim 1, wherein the surface of the handle, at least the distal part of the handle, has a milled finish.

18. The saw guide according to claim 1, wherein the opening of the frame has an angle of 60 degrees.

* * * * *